(12) United States Patent
Coppi

(10) Patent No.: US 8,079,985 B2
(45) Date of Patent: Dec. 20, 2011

(54) GUIDE DEVICE FOR INTRODUCING AT LEAST A SURGICAL INSTRUMENT INTERNALLY OF AN ORGANIC CAVITY, IN PARTICULAR A VASCULAR CAVITY

(76) Inventor: Gioacchino Coppi, Modena (IT)

( * ) Notice: Subject to any disclaimer, the term of this patent is extended or adjusted under 35 U.S.C. 154(b) by 191 days.

(21) Appl. No.: 12/301,940

(22) PCT Filed: May 30, 2007

(86) PCT No.: PCT/IT2007/000378
§ 371 (c)(1),
(2), (4) Date: Nov. 21, 2008

(87) PCT Pub. No.: WO2007/138638
PCT Pub. Date: Dec. 6, 2007

(65) Prior Publication Data
US 2010/0262087 A1  Oct. 14, 2010

(30) Foreign Application Priority Data
May 31, 2006 (IT) .............................. MO2006A0173

(51) Int. Cl.
*A61M 5/178* (2006.01)
(52) U.S. Cl. ..................... 604/158; 604/103.03; 604/528
(58) Field of Classification Search .......... 604/528–529, 604/532, 103.03, 93.01, 158
See application file for complete search history.

(56) References Cited

U.S. PATENT DOCUMENTS
4,774,949 A * 10/1988 Fogarty .......................... 606/108
6,379,319 B1 * 4/2002 Garibotto et al. ............. 600/585

FOREIGN PATENT DOCUMENTS
DE  10201185 A1  7/2003
EP  0132215 A1  1/1985
WO  2006046244 A  5/2006
* cited by examiner Primary Examiner — Kevin C Sirmons
Assistant Examiner — Deanna K Hall
(74) Attorney, Agent, or Firm — Pearne & Gordon LLP

(57) ABSTRACT

A guide device (1) for introducing at least a surgical instrument internally of an organic cavity (2), in particular a vascular cavity comprises a guide body or guide catheter (3) which is substantially hollow and flexible and exhibits an open directing end (8) which is transversal. The device comprises an elongate and flexible guide element (9), which is slidable internally of the guide body (3) to define an advancing guide for the guide body (3). The device (1) also includes means for stabilising (10) for easily piloting the directing end (8) with respect to the transversal cavity (2b) and for advancing the guide catheter. The means for stabilising are defined by a stabilising opening (11) and by an elongate and flexible stabilising element (12) which internally engages the guide body (3) and exits therefrom through the stabilising opening (11) along the cavity occupied by the guide body (3). The stabilising element (12) behaves as a rotation pivot by means of which the operator doing the operation can easily align the directing end (8) of the guide body (3) with the transversal cavity (2b), and guide the directing end (8) into the transversal cavity (2b).

16 Claims, 3 Drawing Sheets

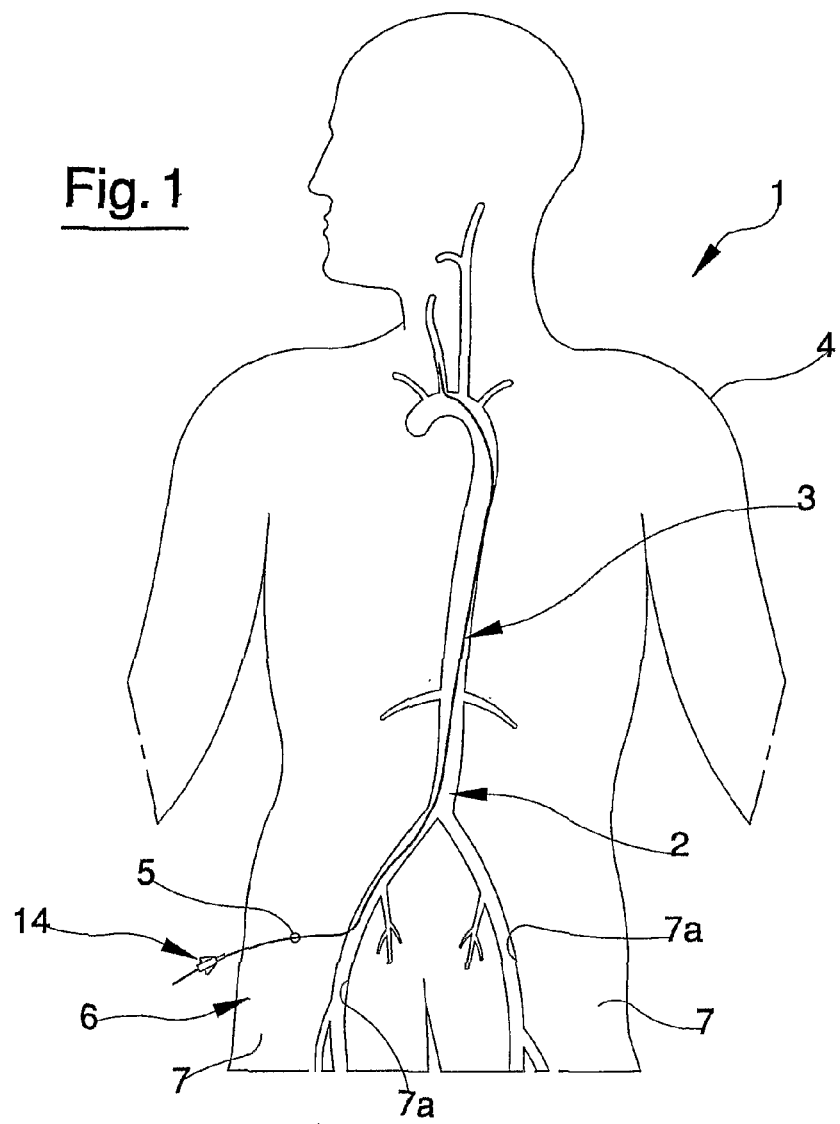
Fig. 1
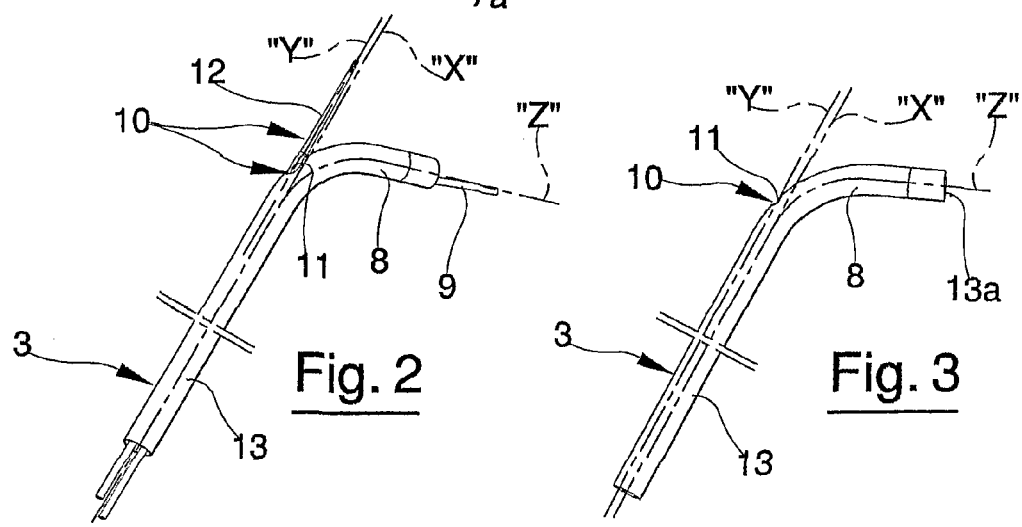
Fig. 2
Fig. 3

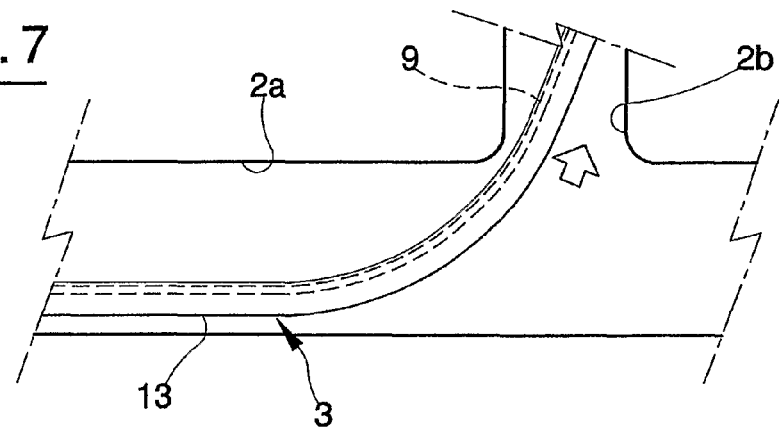
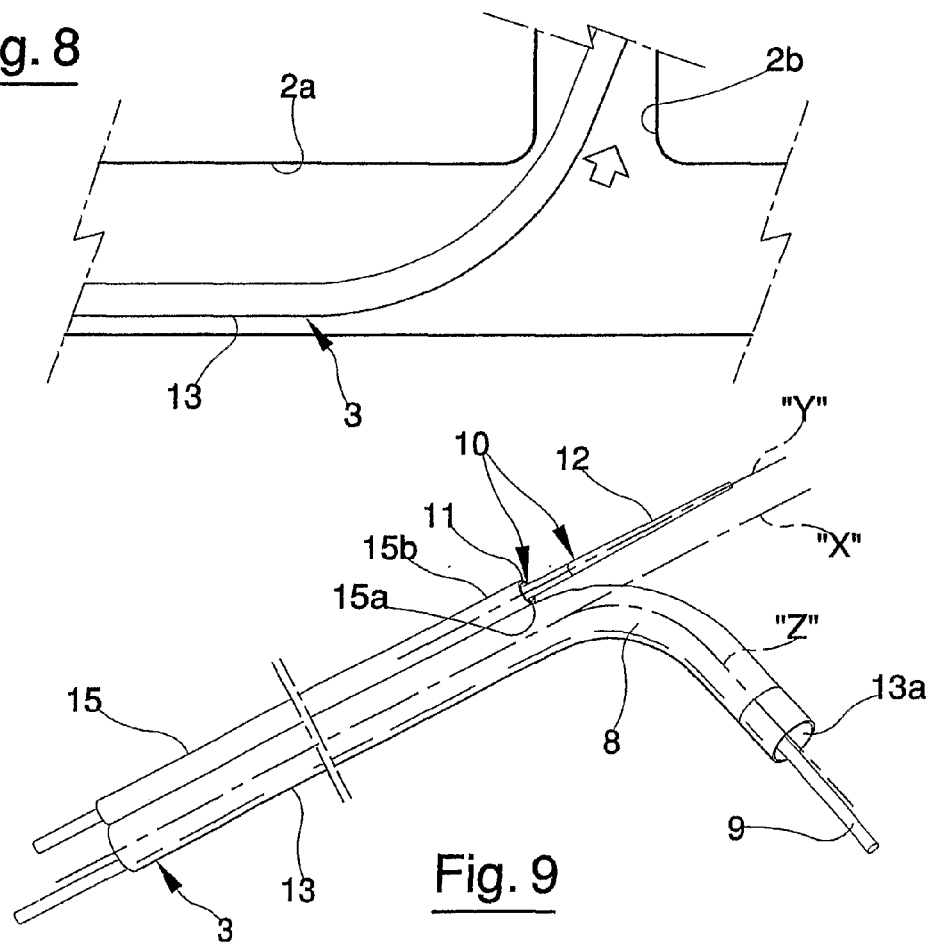

GUIDE DEVICE FOR INTRODUCING AT LEAST A SURGICAL INSTRUMENT INTERNALLY OF AN ORGANIC CAVITY, IN PARTICULAR A VASCULAR CAVITY

TECHNICAL FIELD

The invention relates to a highly-controllable guide device for introducing at least an endoluminal surgical instrument internally of an organic cavity, in particular a vascular organic cavity.

The invention can be usefully applied in the medical-surgical sector, and is in particular used for minimally-invasive operations, such as, for example, angioplasty, endovascular operations, stent implant operations and/or any other type of operation in which spaces are significantly limited and reaching the destination zone requires a high degree of sensitivity and manoeuvring capacity on the part of the surgeon.

BACKGROUND ART

As is known, endovascular operations require the use of one or more guide devices, for example catheters provided with guide wires and/or similar devices which enable surgical instruments to be inserted in the vascular apparatus, such as balloons for angioplasty operations, stents and the like. Generally the known devices comprise an elongate and flexible hollow guide body, exhibiting external transversal dimensions which are smaller than the internal transversal dimensions of the cavities (vessels, veins and/or arteries) destined to receive them.

The hollow guide body exhibits an open directing end, called the distal end, for enabling both the passage of at least a guide wire, destined to advance the guide body internally of the vascular cavities, and one or more endovascular surgical instruments, required for the performing of the surgical operation.

On the opposite side from the directing end of the catheter guide body, means for manoeuvring are provided for moving the guide body internally of the involved vascular cavities, and an open end is provided (called the proximal end) which communicates with the cavity or hole of the catheter which remains external of the insertion and extraction organism through which a guide wire is slid. This end exhibits adaptors for facilitating the manoeuvres of introducing contrast liquids, and for inserting and extracting guide wires to and catheters. By manipulating the proximal end, which is external of the organism, rotation and pushing movements are impressed on the directing distal end for directing the point of the catheter in the desired direction internally of the vessels.

The introduction of the guide body internally of a patient's body requires realising an appropriate passage opening. To perform introduction of these devices special introducing catheters are used, into which the guide catheter can be passed. A mandrel guide catheter (functioning both as an introducer and as a guide catheter) can be used at the starting cavity for the advancing pathway, for reaching the pathology to be treated.

Once the guide body is introduced into the patient's body, the guide body is pushed along one or more of the cavities defining the advancing pathway thereof, following a sliding guide which moves along the whole length thereof and which goes further than it. The guide body is ably oriented internally of the cavities by means of rotation manoeuvres from the proximal end external of the organism, to direct the sliding guide and the guide body catheter around the curves and branches of the organic cavities up until it reaches the desired operating position.

With the aim of enabling better movement of the hollow guide body along the predetermined advancing course, and at the same time facilitating the operator doing the operation at the bifurcations and/or accentuated branching of the cavities, the directing end extends transversally and with various conformations according to the various catheters and the different anatomical needs with respect to the longitudinal development of the guide body.

The advancing of the guide body is accompanied by the use of a guide wire which, being inserted in the guide body, exits through the directing end and covers at least a tract of the transversal vascular cavity, enabling a constrained sliding of the guide body oriented along the guide itself.

Although known guide devices enable the operating site to be reached, the Applicant has noted that they exhibit some drawbacks, mainly in relation to the controlling of the guide body catheter. There are frequent problems of alignment and relating to the stability of the directing end of the guide body with the transversal cavities or branches encountered during the advancing run.

In particular, the Applicant has noted that the aligning of the directing end of the guide body, performed by means of appropriate radiographic viewing devices, is falsified or made difficult by the two-dimensional perception of the advancement run under radioscopy. Consequently, once the directing end has been aligned with the respective involved transversal cavity it is hard to understand, and if necessary correct, in a substantially perpendicular plane to the two-dimensional viewing plane, the inclination of the directing end with respect to the geometrical axis of the respective cavity, both because of the anatomical complexity of the body cavity and due to the instability of the directing end of catheter guides, their not having a sufficient support internally of the cavities. Because of this the directing end can be subjected to large-scale and uncontrollable changes of position due to the rotations and thrusts impressed on the catheter on the proximal part, in the attempt to locate the catheter in the desired position.

In this situation, the operator proceeds by trial-and-error and uses his or her experience and manual dexterity in order to get the guide wire to exit from the guide body, also following the organic cavities around the bends and branches, without striking the internal walls of the involved cavity.

Naturally in any case these drawbacks require a series of manoeuvres of the guide body, leading to a considerable loss of time, with the risk of obtaining a misalignment of the directing end and the involved vascular cavity due to brusque movement of the guide body or the patient, or the flow of organic liquids internally of the cavities, also increasing the risk of damage to the walls of the treated cavities.

Further, in the branching of the vessels, the tactic of first pushing a very flexible guide into the passage of the branch, which flexible guide is internal of the guide body, then to push the guide body itself into the branch to be cannulated, is often unsuccessful because the guide body does not have sufficient flexibility to follow the guide which, among other things, may not provide sufficient support to the guide body catheter. Equally, a less flexible guide introduced before in the branch (in which the guide body is to be introduced) tends to dislodge the guide body, and does not overcome the obstacle.

Finally, in cases where treatment is to be performed on the lesions which are distal of the branch (for example applying a stent), while keeping the guide body at the mouth of the branching vessel, the procedures are always at risk of complications due to the substantial instability of the catheter.

The aim of the present invention is to provide a guide device which is effectively controllable for the introduction of at least a surgical instrument internally of an organic cavity, which simplifies and ensures the aligning operations of the guide body with transversal cavities, facilitating the advancing of the guide body towards the pathology to be reached and treated, even in anatomically complex cases.

A further aim of the invention is to stabilise the guide body during the aligning operations thereof with the involved transversal cavities.

A further aim of the invention is to reduce the times necessary for reaching the pathology to be treated in order consequently to reduce the overall times of the surgical operations in all cases.

DISCLOSURE OF INVENTION

Further characteristics and advantages will better emerge from the detailed description of a guide device for introducing at least a surgical instrument is internally of an organic cavity, in particular a vascular cavity, according to what is claimed herein below.

Further characteristics and advantages of the present invention will better emerge from the detailed description that follows, illustrated by way of non-limiting example in the accompanying figures of the drawings, in which:

FIG. 1 is a schematic view of a guide device for introducing at least a surgical instrument internally of an organic cavity of a patient's body;

FIG. 2 is an interrupted perspective view of a detail of the device of FIG. 1, in agreement with a first embodiment of the present invention;

FIG. 3 is a further interrupted perspective view of the detail of FIG. 2, with some parts removed;

FIG. 7 is a further interrupted schematic view of the device of the preceding figures, represented in a second advancement stage along the transversal cavity;

FIG. 8 is an interrupted schematic view of the device of the preceding figures, represented in a final stage in which the device is located at the pathology to be treated;

FIG. 9 is a perspective view of a detail of the device in a second embodiment of the present invention.

Figure 4:
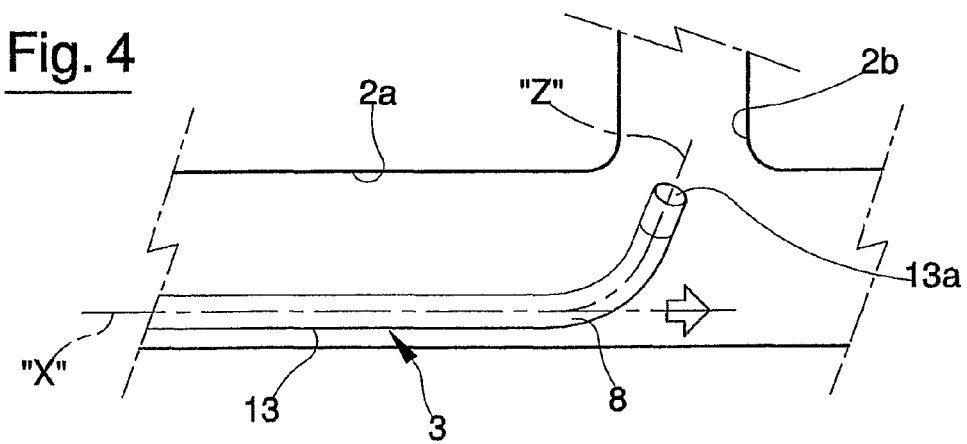
FIG. 4 is an interrupted schematic view of the device of the preceding figures, represented in a first stage of advancement thereof internally of an organic cavity.

With reference to the above-cited figures of the drawings, 1 denotes in its entirety a guide device for introducing at least a surgical instrument (not illustrated as of known type) internally of one or more organic cavities 2, in agreement with the present invention.

As illustrated in the accompanying figures of the drawings, the guide device 1 comprises at least a guide body 3 which is substantially hollow and flexible, which extends along a preferential development direction X.

As can be seen in FIGS. 4-8, the guide body 2 is advantageously engageable internally of a first organic cavity 2a or any organic channel of the human body of a substantially elongate shape, such as, for example, a vascular vessel (a vein or artery) or a similar body channel.

As illustrated in FIG. 1, the guide body 2 can be inserted in the body 4 of a patient through an opening 5, made at a zone 6 identified as an ingress zone. If the device is destined for endovascular operations, such as angioplasty operations, stent implants and similar operations, the ingress zone 6 preferably corresponds to one of the lower limbs 7 of the body 4 of the patient in order to accede, as shown in FIG. 1, to a respective femoral artery 7a. With reference to FIGS. 2-6 and 9, the guide body 3 exhibits a directing end 8 which extends transversally, in various configurations, with respect to the preferential development direction X in order to face the second cavity 2b (FIGS. 4-6), which is transversal of the first cavity 2a.

As illustrated in FIGS. 2, 6, 7 and 9, the device 1 comprises at least a guide element 9 having an elongate and flexible conformation, slidably engageable internally of the guide body and exiting through the directing end 8 to reach the second cavity 2b.

The guide device 1 advantageously comprises means for stabilising 10 (FIGS. 2, 3, 5, 6 and 9) associated to the guide body 9, dedicated to controlling the guide body catheter in order to improve the advancing thereof in the cavity 2a, facilitating the positioning of the directing end 8 with respect to the second cavity 2b and finally facilitating the movement of the guide body in the cavity 2b.

The means for stabilising 10 preferably comprise at least a stabilising opening 11 (FIGS. 2, 3, 5, 6 and 9) afforded through the guide body 3 and at least a stabilising element 12 (FIGS. 2, 3, 5, 6 and 9) which is elongate and very long (preferably beyond 220 cm), preferably filiform and flexible, slidably engageable internally of the guide body 3 in which it is introduced from the outside in proximal direction through the stabilising opening 11, slid along the cavity 2a in order to exit from the proximal end. This manoeuvre is obviously performed when the catheter guide body is external of the organism.

Figure 5:
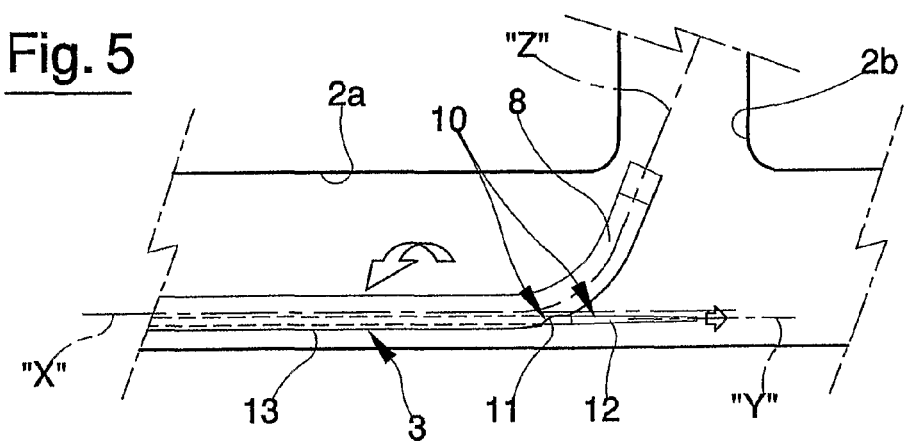
FIG. 5 is an interrupted schematic view of the device of the preceding figures, represented in a stage of alignment with a transversal cavity.
Figure 6:
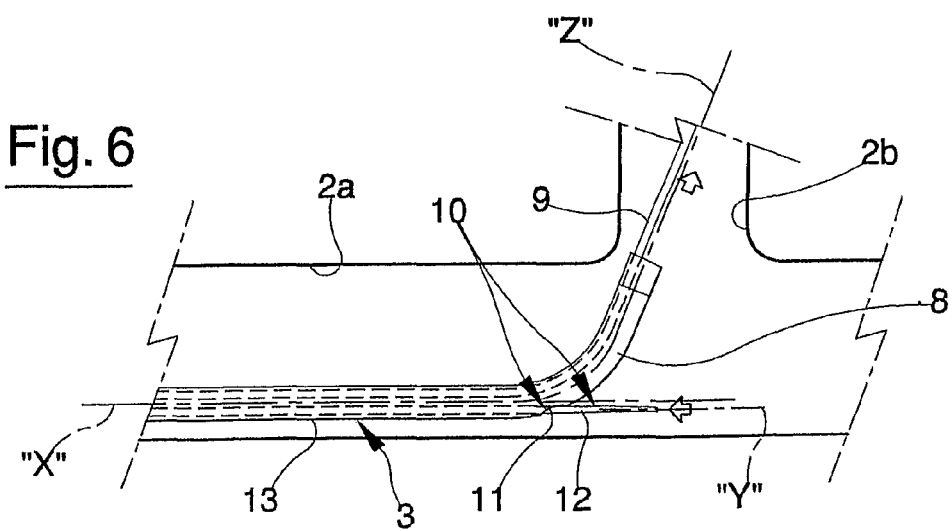
FIG. 6 is a further interrupted schematic view of the device, represented in a following the stage of alignment of FIG. 5.

As can be seen in FIGS. 5 and 6, during the aligning of the directing end 8 with the second cavity 2b, the stabilising opening 11 is facing the first cavity 2a on the opposite side with respect to the guide body 3.

In more detail, when the guide body 3 is engaged internally of the first cavity 2a (FIGS. 5 and 6), the stabilising opening 11 lies on a substantially transversal plane with respect to the preferential development direction X and exhibits a geometric axis Y which extends along the first cavity 2a, substantially parallel to the preferential development direction X.

As can be seen in FIGS. 2, 5, 6 and 9, the stabilising element 12 exhibits transversal dimensions that are smaller than those of the stabilising opening 11 in order easily to cross the stabilising opening 11.

The stabilising element 12 preferably exhibits a structural rigidity which is greater than that of the guide element 9 so that its sliding and presence internally of the guide body 3 causes the exiting thereof through the stabilising opening 11.

This leads to an increase in the supporting capacity and the rigidity of the catheter guide body (which remains stable when the guide element 9 is pushed beyond the directing tract of the catheter 8 into the second cavity (or bifurcating branch 2b).

To this reason the stabilising element 12 can exhibit the same transversal dimensions as a common metal guide (0.035 inches).

In a first embodiment of the present invention, represented in FIGS. 1-8, the guide body 2 exhibits at least a tubular structure 13 defining the open directing end 8 which extends, transversally to the preferential development direction, in a curved direction Z.

With reference to FIGS. 3 and 4, the tubular structure 13 further defines at least an internal guide channel 13a, having a substantially circular section, for sliding the guide element 9 and/or the stabilising element 12 (not illustrated in FIG. 4 but clearly visible in FIGS. 5 and 6), and/or at least a surgical instrument destined for the operation to be performed.

As illustrated in FIGS. 2, 3, 5 and 6, the stabilising opening 11 is preferably arranged between the directing end 8 and suitable means for manoeuvring 14 (FIG. 1) situated on the opposite side to the directing end 8 and deputed to moving the guide device 1.

The stabilising opening 11 is advantageously situated along the tubular structure 13 of the guide body 3 in a substantially aligned position to the preferential development direction X and substantially tangential to the curved development Z of the directing end 8.

As illustrated in FIGS. 2 and 5-7, the guide channel 13a is predisposed to receive slidingly and/or permanently both the stabilising element 12 and the guide element 9, which can also operate singly in the absence of the other element (FIGS. 5 and 7).

In a second embodiment of the present invention, represented in FIG. 9, the guide body 3 exhibits at least an auxiliary tubular structure 15 internally defining at least a stabilising channel 15a having a substantially circular section, dedicated to the sliding and/or the operating permanence of the stabilising element 12.

The auxiliary tubular structure 15 is preferably solidly engaged to the tubular structure 13 of the guide body 3 such that the stabilising channel 15a extends substantially parallel with respect to the guide channel 13a, with the exception of the tract defined by the curved directing end 8.

In the preferred conformation the tubular stabilising structure terminates at the position of the curved directing end 8 of the guide body 10 (see FIG. 9) but in a further configuration the stabilising structure can be advantageously much longer in order to facilitate guide change manoeuvres which are non-traumatic for the vessels.

In the further embodiment the stabilising opening 11 is in fact a terminal end 15b of the auxiliary tubular structure 15 and is arranged between the directing end 8 of the tubular structure 13 and the means for manoeuvring 14 (FIG. 1). The auxiliary tubular structure 15 advantageously exhibits transversal dimensions which are smaller than the transversal dimensions of the tubular structure 13, as it is only destined to receive the stabilising element 12 operatively.

As illustrated in FIG. 1, when the guide device 1 is used for endovascular operations such as angioplasties, stent implants and the like, the guide body 3, together with the guide elements 9 and stabilising (and controlling elements 12) is inserted into the body 4 of the patient under treatment in order to reach the vascular zone interested by the pathology. These elements can be used in various combinations according to need and advantage.

Naturally, the guide device 3 of the present invention can be used for any low-invasive surgical treatment of pathologies which involve different parts of the organisms from the vessels, such as for example pathologies relating to the urinary apparatus, the digestive system, the kidneys and/or any other apparatus which can be reached by means of the above-described guide device 1.

As illustrated in FIGS. 4-8, when the guide device is introduced into the body 4 of the patient, in order to treat any type of pathology, with the aid of special viewing means, the operator manoeuvres the guide body 3 along a predetermined tortuous advancing path with the help of the sliding elements 9 and the stabilising elements 12 previously inserted in the guide body. The advancing of the guide body 3 requires continuous changes of direction at which collaboration between the guide body 3, the guide element 9 and the stabilising element 12 considerably facilitates reaching the site of the pathology.

In particular, when the guide body 3 is at a place necessitating a sharp change in direction, such as for example the situation illustrated in FIGS. 4-8, in which the guide body has to transit from a first cavity 2a to a second cavity 2b which is transversal to the first cavity 2a, the guide body 3 is made to advance on the axis of the stabilising element 12 positioned such as to engage the first cavity 2a beyond the second branch cavity 2b and with the sliding element 9 which can exit from the distal apex of the guide body when the directing end 8 is in proximity of the second cavity 2b (FIG. 4). The sliding element 9 is retracted such as to leave the lumen 13a of the cross tract of the guide body free. In this way the stabilising element 12 constitutes a prolongation of the guide body 3 along the first cavity 2a, taking on the function of rotation pivot of the guide body 3 (FIG. 5). At this point, the guide body 3 can be specially rotated about the stabilising element 12 in order to enable a correct and controlled alignment of the directing end 8 with respect to the second cavity 2b (FIG. 5).

In this situation, the guide body 3 is kept still while the stabilising element 12 is introduced into the guide body 3 in order to exit therefrom through the stabilising opening 11.

When alignment has been achieved, the guide element 9 is introduced into the guide body 3, is newly pushed into the guide body in order to exit from the guide body 3 through the directing end 8. The guide element 9 then inserts into the second cavity 2b, running along at least a significant tract thereof (FIG. 6), having the solid support of the guide body established by the stabilising element 12.

Thereafter the procedure can be performed in two different ways. In the first way, when the guide element 9 is well past the branching of the cavity 2b and it is felt that it can offer sufficient support for the sliding of the guide body 3, the stabilising element 12 is extracted from the guide body 3 in order to enable the guide body 3 to proceed along the advancing pathway in the cavity 2b, following the guide element 9 (FIG. 6). Alternatively a guide-changing catheter is introduced onto the sliding guide, which sliding guide is substituted by a more rigid guide on which the catheter is pushed.

In the second way, when the guide element 9 is well past the branching of the cavity 2b, but it is felt that it cannot provide sufficient support for the sliding of the guide body 3, the stabilising element 12 is retracted into the distal apex in the lumen 13a of the guide body and is then newly pushed upwards, preventing it from newly engaging the outlet hole 11 but making it follow the same pathway as the guide element 9 supported by the stabilising element 11 already positioned.

Once the two guides (sliding and stabilising) are properly positioned beyond the cavity 2b, the guide body can be advanced in the transversal cavity 2b exploiting the strong support the two guides give.

The above-described operations (FIGS. 4-7) are repeated each time the guide body 3 needs to make a brusque change of direction; once a first bifurcation has been negotiated, with the guide element 9 and the stabilising element 12 located high in the guide element 9 projecting from the distal lumen 13a, the catheter is extracted, leaving the guides in position, and then re-introduced with the guide entering from the distal lumen 13a and the stabilising element 12 which passes through the opening 11. In this way the catheter is moved up and reset in order to negotiate a further branching.

When the desired position for treatment of the lesion has been reached (FIG. 8), the guide body 3 is kept still and the guide element 9 and the stabilising element 12 are disengaged therefrom in order to enable sliding of the surgical instrument with the catheter opening completely free.

In other cases, with the guides left in place, the guide catheter is extracted and replaced with an introducer of a desired shape or by other operative catheters of the MoMa type (produced by Invatec Srl, Roncadelle (BS), Italy).

The guide device of the present invention resolves the problems encountered in the prior art and provides important advantages.

Firstly, the guide device of the present invention considerably facilitates the aligning operations of the guide device with the transversal cavities encountered along the pathway of the guide towards the pathology to be treated.

In particular, the presence of the above-mentioned means for stabilising enable a rapid and correct alignment of the directing end of the guide body with the transversal cavities of the advancing pathway even when the angle below the occupied cavity of the guide device and the transversal cavity to be entered is a right angle or an acute angle.

Consequently, the present invention enables a rapid reaching of the zone to be treated, determining a large reduction in the operation times. The operator is no longer forced to proceed by trial and error, as the device is very highly controllable and is the fruit of very precise and effective technology.

In a preferred embodiment the stabilising opening 11 must be placed just upstream of the start of the distal curvature of the guide body, or transversal tract of the catheter 8, so that there is no difficulty in introducing the stabilising element 12 from outside into the catheter opening (in a proximal direction), while it is not advantageous for any guide to be engaged therein in arrival from the proximal end. This configuration enables the stabilising guide 12, after having supported the guide element 9 in its rise in the bifurcated branch, to be retracted into the opening of the catheter 8 and to be then pushed, following the distal curve of the catheter 8 in the bifurcation branch 2b, where the guide element 9 is already situated. This is to provide a strong support for the catheter 8, preventing the stabilising element 12 from further engaging in the stabilising opening 11.

In a preferred embodiment, the stabilising opening 11 can be evidenced with at least a radio-opaque marker which helps the operator to prevent the stabilising element 12 from engaging in the opening 11, or which enables the stabilising element 12 to be re-introduced therein. The radio-opaque marker is also for precisely locating the position of the stabilising opening 11 during the is procedure.

In a further embodiment, the stabilising opening 11 is located in the same direction as the straight main axis of the catheter 8.

In a further embodiment, the stabilising opening 11 of the catheter 8 can exhibit means for closing. The means for closing enable the stabilising element 12 to be introduced in the opening from the outside towards the inside, preventing an oppositely-directed passage.

In a further embodiment, the means for closing are represented by strips which can be neared to one another until they are side-by-side, and which are elastically deformable at least around the stabilising opening 11.

The strips are elastically conformed such as to conform to the original profile, i.e. the profile of the catheter itself, when the stabilising opening is not engaged by the stabilising element 12.

In a further embodiment, the means for closing are represented by valve which is applied, as an accessory element, to the stabilising opening 11.

In any case the function devolved to the means for closing is to enable passage of a guide from the outside, through the stabilising opening 11 and not the opposite.

The catheter 8 can be inserted in a vessel by means of a introducer catheter. In a further embodiment the introducer catheter can be omitted. In this embodiment, an access valve and a tubular element are situated proximally, which valve and tubular element communicate with the lumen 13a for introduction of liquids, as in known introducers. A mandrel can be added, having two openings of which one stretches over the whole length thereof and another, more lateral (it can be a simple groove) allows, in proximity of the apex, an alignment with the stabilising opening 11. The distal end of this mandrel exhibits a smaller diameter than that of the lumen 13a in order for it to be introduced and removed with the stabilising element 12 in place.

In a preferred application the described device is used for applications in the carotid.

The prior art in PTA/carotid stenting represents a valid alternative to carotid TEA (surgical destruction), but access to the super-aortic/carotid trunks often represents a grave difficulty and is one of the most common causes of complications and failures in the procedure.

At present this is done by the use of numerous angiographic catheters of different configurations in order to search for and overcome the different anatomies which are the more complex the older the patient with advanced arteriosclerosis, which are exactly the situations in which a less invasive technique is most needed.

In usual procedures an angiographic catheter is brought, with a hydrophilic guide, to the ostium of the super-aortic vessel; the guide is removed and the vessel is identified by the angiography. An attempt is made to apply the catheter to the initial part of the vessel which is then incannulated by the re-introduced hydrophilic guide, on which the catheter is advanced up into the desired vessel (usually in the external carotid); the hydrophilic guide is replaced with a strong supporting guide (stiff or superstiff), the angiographic catheter is removed and a guide catheter or a MoMa catheter (produced by Invatec Sri, Roncadelle (BS), Italy) is introduced, on which the PTA/stenting manoeuvres will be performed. These manoeuvres require, in all cases, considerable experience and become difficult, if not impossible, in cases of anatomical variation, even for expert operators, because of the increase in the angulations of the bends and curves.

In simple cases too it is often necessary to perform uncontrolled manoeuvres several times with the catheters in the aortic arch, with the risk of dislodging thrombi; the presence of even slight curves in the downstream vessels, which nonetheless offer resistance to the movement of the guides and catheters, tends to dislodge the catheters and guides suddenly and violently, due to the different and conflicting pull-and-thrust directions between the guide catheters and vessels.

In the attempt to overcome these difficulties, various techniques have been suggested, such as the use of long introducers or guide catheters which provide greater support to angiographic catheters and/or the application of double guide catheters (the buddy wire technique). These manoeuvres are however very complicated and do not overcome the main problem which is how to take a guide with good support very distally in order to be able to perform the following movements. The basic lack is an initial rest base in the aorta which enables simple and controlled manoeuvres to be performed and lends the sliding element 9 stability and adequate support for it to be taken into the desired position, and also provides the guide catheter a support so that it can be introduced in the common carotids in proximity of the bifurcation.

One of the main objectives of the invention described herein is to obviate the above difficulties at this level, using the above-described guide body catheter system and two guides, of which one has a support function and pivot (the stabilising element 12) and the other has an access and support function (the sliding element 9).

The main configuration of the distal part of the guide body at this level is a hook shape with a slightly counter-curved distal end; the proximal shoulder of the curvature (just distal of the lateral hole) must give, for a length of some millimeters, good support in order to be able to direct the guides (9 and 12) is while the rest of the guide body catheter 3 both upstream and downstream of the above-described tract must be very flexible and twistable (to negotiate the curves) while stiffness is not required, as the support is guaranteed by the stabiliser guide 12.

With the use of 0.0035 guides, a French (F) 7 guide catheter is required.

The procedure is performed as follows.

Inguinal access with 30-45 mm 8-9 F introducer. Two long guides, one superstiff or stiff and termed the stabilising element 12 and one hydrophilic, floppy or stiff, termed the sliding element 9, are applied through the introducer; the stabiliser element 12 is brought to the ascending aorta while the sliding element 9 can be kept in the descending aorta. Then the guide catheter is readied and the stabilising element 12 is introduced through the stabilising opening 11 of the guide catheter from the outside, and made to exit proximally, while the sliding element 9 is passed through the apex and is made to exit proximally too. The catheter is then passed into the aorta through the introducer and raised upwards in the arch, keeping the guides still and the point of the guide body catheter turned (transversal part 8) towards the aortic lumen in order to prevent the apex from touching against the aortic wall and mobilising thrombi. Once in proximity of the vessel to be incannulated, identified by the angiography through the guide body catheter (without removing the guides) the catheter is rotated, pivoting on the stabilising element 12 in order to locate with the ostium thereof distal of the initial part of the vessel to be incannulated, the stabilising element 12 being kept very stable. Using angiographic controls or road-mapping, the sliding element 9 is pushed high into the super-aortic vessel (usually into the external carotid). This manoeuvre, complex and risky in many cases, is made safe by the support of the stabilising element 12. At this point the stabilising element 12 is retracted into the lumen of the catheter just proximal of the lateral hole and is then pushed once more high into the vessel to be treated; this is facilitated by the support provided by the sliding element 9, already high up in the vessel, exchanging the support initially provided by the stabilising element 12. It is easy at this point to push the guide catheter into the desired vessel as it is supported by two well-supported guides. This manoeuvre is easily applied in complex anatomies too, and can be used by operators of limited experience.

In the case of bovine arches, where the internal left carotid is to be reached, this manoeuvre can be performed twice; once for reaching the anonymous artery, and a second in which the guide catheter is extracted and reintroduced with the guide very well supported entering from the lateral hole and the hydrophilic guide entering from the distal lumen. With the guide catheter returned to high up in the anonymous artery, the hydrophilic guide is retracted into the guide catheter and the guide catheter (with the apex medialised) is slightly in front of the ostium of the left common carotid, repeating the above-described manoeuvres by adjusting the two guides. This procedure makes the treatment of these cases, up to now excluded or performed only by very great experts with considerable risk, accessible to less expert operators. The described catheter can also be used for other minimally-invasive operations.

For example, it can be used in complex neuro-surgical or carotid bifurcations. In this application, with the rest-guide and access-guide principle remaining the same, by using 0.0018-inch, 0.021-inch or 0.0014-inch guides the guide catheters can be reduced to 3-6 F and with vertebral type design all the difficult forks can be progressively negotiated with adequate support.

For example, the invention can be used in aorto-coronary by-passes.

In this application, with the rest-guide and access-guide principle remaining the same, solutions can be sought with catheters of adequate length and smaller caliber and wider or sharper curves angled according to an access from the upper limbs or the groin. Using 0.0018-inch, 0.021-inch or 0.0014-inch guides the guide catheters can be reduced to 3-6 F.

For example, the invention can be used in mammary operations.

In this application the degree of curvature and the length of the curved tract must be especially small in order to be able to rotate internally of the succlavia vein.

For example the invention can be used in the thoracic aorta. In this application an angiographic catheter with a support guide is very much suitable for a rapid examination of the intercostal, lumbar and visceral arteries, as it can perfectly control the position of the catheter apex (the catheter moves as if on a support wire). This enables performance of simple angiographic examinations at desired levels and in a desired direction (the support catheter functions as a pivot and the contrast fluid exits only from the apex, as the lateral lumen is occluded by the support guide), and also enables a characterisation to be made of the desired vessel using the double-guide method already described for the carotid.

The invention can be used, for example, in kidney operations. In this application, using adequately-curved catheters it is possible to perform renal angioplasty operations using the no-touch technique. With a single guide catheter it is possible to position the guide catheter in the aorta by approaching the renal artery with guides exiting from the apex, preventing the guide from damaging the aortic wall.

The invention can be used, for example, in the aorta-illiac and femoral fork. In this application, with a similar catheter with axes of curvature and lengths of the curved tract which are adequate, and using the play between the two guides, it is easy to negotiate all of the possible difficult angulations, and is also easy to obtain rest points for the access guide in the attempt to channel occluded tracts of artery.

The invention claimed is:

1. A guide device (1) for introducing at least a surgical instrument internally of an organic cavity (2), the device (1) comprising:
    a guide body (3) which is substantially hollow and flexible and extends along a preferential development direction (X) and which exhibits an open directing end (8) which is transversal to the preferential development direction (X), the guide body (3) being engageable internally of a first cavity (2a) for positioning the directing end (8) facing a second cavity (2b), transversal to the first cavity (2a);

at least an elongate and flexible guide element (9), which is slidably engageable internally of the guide body (3) for reaching the second cavity (2b), means for stabilising (10) associated to the guide body (3), which means for stabilising (10) cooperate with the first cavity (2a) to facilitate the positioning of the directing end (8) with respect to the second cavity (2b), said means for stabilising (10) comprising:

at least a stabilising opening (11) afforded in the guide body (3); at least an elongate and flexible stabilising element (12), slidably engageable internally of the guide body (3) in order to exit therefrom in a direction along the first cavity (2a), through the stabilising opening (11), characterised in that the guide body (3) exhibits at least a tubular structure (13) defining the open directing end (8) and internally defining a guide lumen (13a) for sliding the guide element (9) and/or at least a surgical instrument, the stabilising opening (11) being arranged between the directing end (8) and means for manoeuvring (14) arranged on the opposite end to the directing end (8) and moving the guide device (1), the guide lumen (13a) being effective to slidingly and operatively receive the stabilising element (12) and the guide element (9) at the same time.

2. The device of claim 1, characterised in that the stabilising opening (11) faces in a direction of the first cavity when the guide body (3) is engaged internally of the first cavity (2a).

3. The device of claim 1, characterised in that the stabilising opening (11) exhibits a geometric axis (Y) extending along the first cavity (2a) such that the stabilising opening (11) lies on a transversal plane with respect to the first cavity (2a).

4. The device of claim 1, characterised in that the stabilising element (12) exhibits a substantially filiform conformation.

5. The device of claim 1, characterised in that the stabilising element (12) exhibits a greater structural rigidity than a structural rigidity of the guide element (9).

6. The device of claim 5, characterised in that the directing end (8) of the tubular structure (13) extends transversally in a curved direction (Z), with respect to the preferential development direction (X).

7. The device of claim 6, characterised in that the stabilising opening (11) is situated in the tubular structure (13) in a substantially aligned position to the preferential development direction (X) and is substantially tangential to the curved direction (Z) of the directing end (8).

8. The device of claim 1, characterised in that the stabilising opening (11) exhibits means for closing which permit passage of a guide in a direction going only from outside towards inside.

9. The device of claim 8, characterised in that the means for closing comprise limbs which can be located side-by-side and which are elastically deformable at least in a vicinity of the stabilising opening (11).

10. The device of claim 8, characterised in that the means for closing are constituted by a valve applied on the stabilising opening (11) which enables passage of a guide.

11. The device of claim 1, characterised in that close to the stabilising opening (11) there is at least a radio-opaque marker.

12. The device of claim 1, characterised in that the guide lumen (13a) is a bi-directional valved lumen and wherein the device exhibits the bi-directional valved lumen (13a) and a lateral tubular element in communication with a lumen for injection of liquids.

13. The device of claim 1, characterised in that the device comprises a mandrel-catheter which is an accessory of the tubular structure (13), which mandrel-catheter is constituted by a tapered-end tubular element which is longer than the tubular structure (13), which tubular element projects from the distal end of the guide body (3) when inserted therein and having an external diameter which is equal to an internal diameter of the guide lumen (13a), the mandrel-catheter having a two-lumen mandrel function for sliding and stabilising guides.

14. A method of use of a guide device (1) for introduction of at least a surgical instrument internally of an organic cavity (2), the device (1) comprising:

a guide body (3) which is substantially hollow and flexible and extends along a preferential development direction (X) and which exhibits an open directing end (8) which is transversal to the preferential development direction (X), the guide body (3) being engageable internally of a first cavity (2a) for positioning the directing end (8) facing a second cavity (2b), transversal to the first cavity (2a);

at least an elongate and flexible guide element (9), which is slidably engageable internally of the guide body (3) for reaching the second cavity (2b);

the guide device (1) further comprising means for stabilising (10) associated to the guide body (3) and cooperating with the first cavity (2a) for facilitating the positioning of the directing end (8) with respect to the second cavity (2b);

the means for stabilising (10) comprising:

at least a stabilising opening (11) afforded through the guide body (3);

at least an elongate and flexible stabilising element (12), which is slidably engageable internally of the guide body (3) in order to exit therefrom in a direction along the first cavity (2a) through the stabilising opening (11), wherein the guide body (3) exhibits at least a tubular structure (13) defining the open directing end (8) and internally defining a guide lumen (13a) for sliding the guide element (9) and/or at least a surgical instrument, the stabilising opening (11) being arranged between the directing end (8) and means for manoeuvring (14) arranged on the opposite end to the directing end (8) and moving the guide device (1), the guide lumen (13a) being effective to slidingly and operatively receive the stabilising element (12) and the guide element (9) at the same time, characterized in that the method includes the following stages:

inguinal access with an introducer;

use of two long guides, the stabilising element (12) and the guide element (9) being applied through the introducer, in which:

the stabilising element is brought into the ascending aorta, while the guide element (9) is kept in the descending aorta;

the stabilising element (12) is introduced through the stabilising opening of the guide body from the outside and is made to exit proximally;

the guide element (9) is made to pass through an apex and also exits proximally;

the guide body is made to pass into the aorta through the introducer and is made to rise within the arc, keeping the guides still and keeping a point of the guide body rotated towards the lumen of the aorta in order to prevent the point from touching against the aortic wall and moving thrombi;

in proximity of the vessel to be incannulated, identified by an angiography through the guide body without removal of the guides, the guide body is rotated, pivoting on the stabilising element (12) such as to locate with a distal ostium thereof at an initial part of the vessel to be incannulated, where it is held stably by the stabilising element (12);

using angiographic controls or road mapping the guide element (9) is pushed well into the super-aortic vessel;

the stabilising element (12) is retracted into the guide lumen as soon as it is proximal to the lateral lumen and is then pushed up into the vessel to be treated; this is facilitated by the support offered by the guide element (9) which is already high up in the vessel, replacing the support initially provided by the stabilising element (12);

the guide body is pushed into the vessel.

15. The device of claim 1, wherein the organic cavity is a vascular cavity.

16. The method of claim 14, wherein the organic cavity is a vascular cavity.

* * * * *